United States Patent [19]

Latham, Jr.

[11] 4,059,108

[45] Nov. 22, 1977

[54] PROCESS FOR PHERESIS PROCEDURE AND DISPOSABLE PHERESIS BOWL THEREFOR

[75] Inventor: Allen Latham, Jr., Jamaica Plain, Mass.

[73] Assignee: Haemonetics Corporation, Natick, Mass.

[21] Appl. No.: 596,148

[22] Filed: July 15, 1975

Related U.S. Application Data

[63] Continuation-in-part of Ser. No. 497,558, Aug. 15, 1974, abandoned.

[51] Int. Cl.$^2$ .................... A61M 5/00; B04B 11/00

[52] U.S. Cl. .................... 128/214 R; 128/214 D; 128/272; 233/17; 233/32; 233/47 R

[58] Field of Search .................... 233/1 R, 26, 27, 28, 233/17, 18, 32, 20 R, 47 R; 128/214 D, 2 F, 272, 214 R

[56] References Cited

U.S. PATENT DOCUMENTS

| | | | |
|---|---|---|---|
| 3,185,154 | 5/1965 | Caccavo et al. | 233/26 X |
| 3,353,378 | 11/1967 | Kahn | 233/18 X |
| 3,545,671 | 12/1970 | Ross | 233/26 |
| 3,719,182 | 3/1973 | Rose | 128/1 R |
| 3,908,893 | 9/1975 | Williams | 233/20 R |

FOREIGN PATENT DOCUMENTS

| | | | |
|---|---|---|---|
| 2,006,054 | 8/1971 | Germany | 128/214 D |
| 466,290 | 10/1951 | Italy | 233/18 |
| 13,981 of | 1889 | United Kingdom | 233/32 |

*Primary Examiner*—George H. Krizmanich
*Attorney, Agent, or Firm*—David E. Brook

[57] ABSTRACT

A pheresis process and apparatus for carrying it out. Blood from a donor is transferred to a pheresis bowl formed to have a red cell reservoir and a plasma reservoir in fluid communication through plasma ducts. The pheresis bowl is adapted for centrifuging to separate the red cells and plasma. This separation is accomplished simultaneously with the withdrawal of blood from the donor. At the end of the withdrawal the red cells are returned to the donor. The connection with the donor is thus continuously maintained during the entire procedure. The process is safe, fast and economical.

31 Claims, 22 Drawing Figures

PROCESS FOR PHERESIS PROCEDURE AND DISPOSABLE PHERESIS BOWL THEREFOR

This application is a continuation-in-part of application Ser. No. 497,558 filed Aug. 15, 1974, now abandoned.

This invention relates to a pheresis procedure and apparatus therefor. More particularly this invention relates to a disposable plasma pheresis bowl suitable for separating plasma from red blood cells in a pheresis procedure and for returning all of the red blood cells directly to the donor while maintaining direct connection to the donor throughout the procedure.

In the commercial preparation of plasma fractions, for example anti-hemophilic factors, large quantities of frozen plasma are required. In a pheresis procedure the whole blood, drawn from the donor, is immediately separated into plasma and red cells and the red cells returned to the donor. The plasma is then frozen and shipped to fractionation houses. Since the donor's system can readily regenerate plasma, in contrast to the extended period of time required to regenerate red blood cells, it is customary to take two units of blood (2 pints) from the donor and return the red cells to him. The blood factors, such as the anti-hemophilic factor, are labile and great care must be exercised in handling the blood and the plasma fraction to retain the efficacy of these factors. It is also, of course, absolutely necessary that the red blood cells returned to the donor are his own red blood cells.

In the presently used pheresis procedure, whole blood is withdrawn from the donor into a satellite pouch system which consists of one large bag sized to take a pint of whole blood, containing added anticoagulant, and one small bag attached to the large bag. After connection with the donor is broken, the pouch is placed in a bucket-type centrifuge, spun for a few minutes and then removed from the centrifuge without disturbing the plasma/red cell distribution in the large bag. The pouch is then placed in a plasma compressor to express the plasma through a tube into the small bag. The tube to the small bag is closed off and it is severed from the larger bag containing the red blood cells. These red blood cells are then returned to the donor by making a new connection with the donor. The procedure may be repeated again to obtain two units of plasma from a donor at one time.

This prior art method has several serious disadvantages, among which are the danger to the donor that his own red blood cells will not be returned to him; the requirement that blood withdrawal, centrifuging, and plasma/cell separation be carried out as distinct, successive steps thus prolonging the time required; the necessity to use specially trained technicians; and the possibility of destroying at least a part of the efficacy of the blood factor to be derived from the plasma. In addition, the use of a centrifuge rotor with a pump and harness system such as shown for example in U.S. Pat. No. 3,565,286 would be too expensive to use for a pheresis system of the type herein contemplated and would not lend itself to the essentially complete recovery and return of the red cells to the donor.

It would therefore be desirable to have available a process and apparatus for carrying out the blood pheresis procedure which provides a fail-safe procedure which may be rapidly performed by technicians trained in general phelbotomy procedures to obtain a plasma fraction of improved quality.

It is therefore a primary object of this invention to provide an improved pheresis process. It is another object to provide a process of the character described which, by carrying out withdrawal of blood simultaneously with separation of the plasma from the red blood cells, materially reduces the time required to carry out the process. Yet another object of this invention is to provide a fail-safe pheresis procedure which maintains a continuous connection with the donor throughout the entire procedure and thus ensures that the donor's own red blood cells are returned to him. It is a further object to provide a pheresis procedure which makes it readily possible to return essentially all of the red cells to the donor. An additional object is to provide a blood pheresis procedure which requires less handling of the blood thus improving the quality of the plasma obtained, and which can be carried out by general technicians and at a lower cost.

It is another primary object of this invention to provide improved apparatus for carrying out blood pheresis procedures. A further object is to provide apparatus of the character described which makes it possible to carry out whole blood withdrawal from the donor simultaneously with the separation of the plasma and red blood cell fractions, thus materially reducing the time required. Still another object is to provide pheresis apparatus which makes it possible to maintain connection with the donor throughout the procedure thus ensuring the return to the donor of his own red blood cells. A further object is provide pheresis apparatus which ensures the return of essentially all of the red cells to the donor. An additional object of this invention is to provide pheresis equipment of the character described which is capable of improving the quality of the blood factor obtained from the plasma, which reduces the time required to complete the procedure and which reduces the cost of the procedure.

Other objects of the invention will in part be obvious and will in part be apparent hereinafter.

In the process of this invention, whole blood is withdrawn from the donor, with simultaneous addition of an appropriate amount of anticoagulant, and pumped through a tubing extending from the phelbotomy needle in the donor's vein, through a rotary seal, to the bottom of a red cell reservoir which is rotated at centrifuge speed as blood is delivered to it. In the centrifuging, the plasma fraction is separated and transferred to a plasma reservoir which is affixed to the red cell reservoir and spun with it. Shortly after a unit of whole blood has been withdrawn from the donor the centrifuging of the joined reservoirs is stopped and the red blood cells are returned directly to the donor with whom the connection through the tubing and needle has been maintained throughout. The procedure may be repeated by introducing another unit of blood into the red cell reservoir, thus accumulating an additional unit of plasma in the plasma reservoir. After all of the red cells have been returned to the donor, the tubing and needle connection is broken in the usual manner and the plasma reservoir is sealed off and severed from the empty red cell reservoir which is discarded. The plasma is then frozen in the reservoir in which it was collected or in a special container to which it has been transferred.

In brief, the apparatus of this invention comprises a disposable plasma pheresis bowl having a red cell reservoir and a plasma reservoir joined through one or more plasma ducts, the reservoirs and ducts forming one unitary centrifuge rotor. The rotor may be blow molded or otherwise formed by appropriate plastic fabrication techniques from sheets of plastic and sealed over areas of contact on a plane in the axis of rotation. Form-fitting shoe means may be used to support the rotor during centrifuging.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated by the claims.

For a fuller understanding of the nature and objects of the invention, reference should be had to the following detailed description taken in conjunction with the accompanying drawings in which FIG. 1 is a somewhat diagrammatic view of a pheresis system embodying the method and apparatus of this invention;

Figure 1:
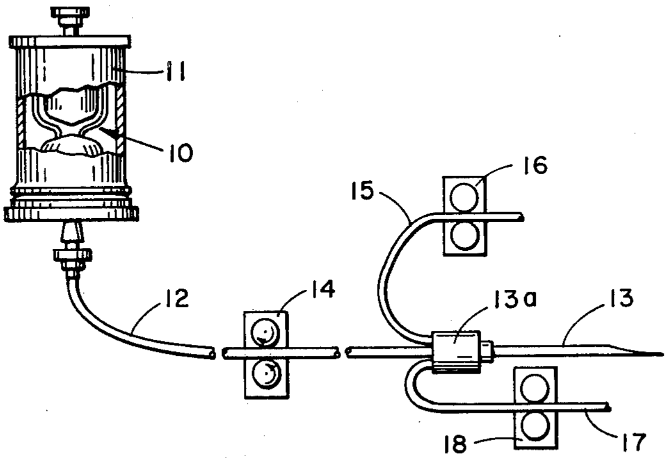
Figure 11:
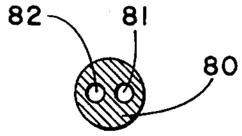
FIG. 11 is a transverse cross section of the vent tube of FIG. 10 taken through section 11—11 of FIG. 10.

FIG. 1 is a somewhat diagrammatic illustration of a pheresis system embodying the pheresis bowl of this invention generally indicated by the reference numeral 10. This bowl 10, contained within a supporting shoe member 11, is connected through tubing 12 to a phlebotomy needle 13 suitable for making a venipuncture. The blood as it is withdrawn from the donor is pumped, by way of a rotary seal, into bowl 10 by a pump 14 which may be any type of pump suitable for handling blood. Exemplary of such a pump is a roller-type pump such as illustrated in FIG. 11 of U.S. Pat. No. 3,565,286. The phlebotomy needle 13 is preferably of a type which has means for introducing an anticoagulant into the blood immediately upon its withdrawal from the donor. Such a needle is described in my copending application Ser. No. 464,835 filed Apr. 29, 1974. The anticoagulant from a source (not shown) is introduced into the needle 13 through tubing 15 connected through needle hub 13*a*, and its flow rate is controlled by pump 16 which may also be of the roller type. If desired, the needle 13 may also be connected through its hub 13*a* to a source of a saline solution or other volume extender (not shown) through tubing 17 having pump 18 associated therewith.

One embodiment of the pheresis bowl 10 of this invention is illustrated in detail in FIGS. 2-8 in which the same reference numerals are used to refer to the same apparatus components.

Figure 2:
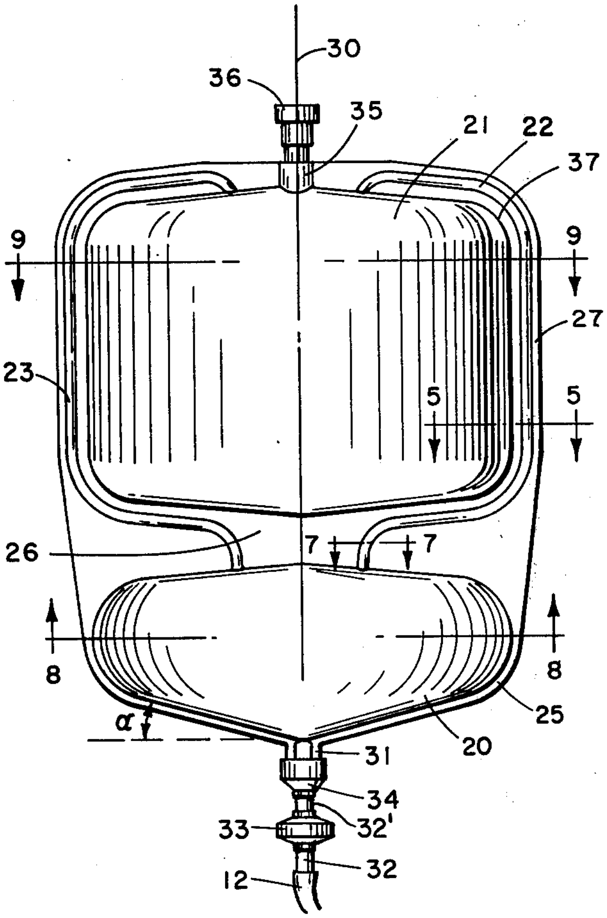
FIG. 2 is a front elevational view of one embodiment of the disposable plasma pheresis bowl of this invention.
Figure 3:
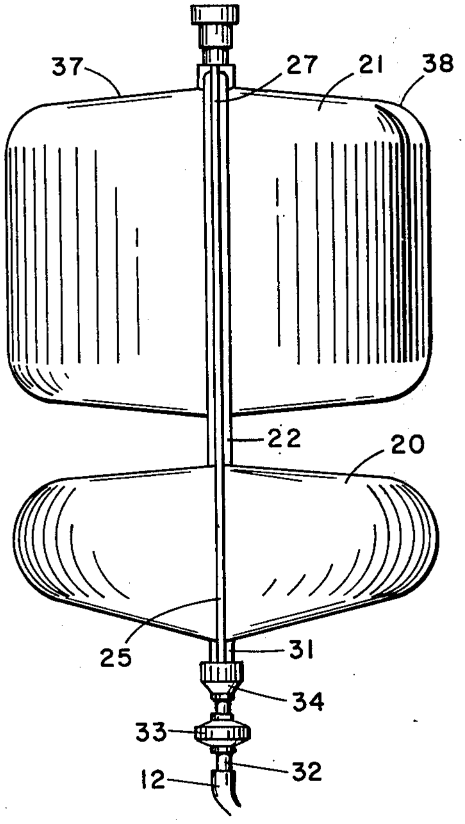
FIG. 3 is an end elevational view of the disposable plasma pheresis bowl of FIG. 2.
Figure 5:
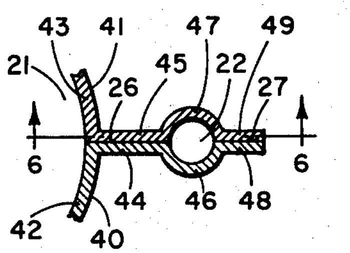
FIG. 5 is an enlarged cross section through the wall of the plasma reservoir and a plasma duct of the embodiment of FIG. 2 taken through plane 5—5 of FIG. 2.
Figure 6:
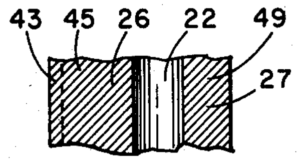
FIG. 6 is a cross section of the wall of the plasma reservoir and a plasma duct taken through plane 6—6 of FIG. 5.
Figure 7:
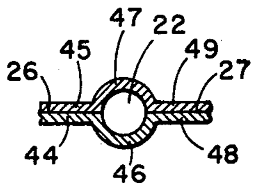
FIG. 7 is a cross section of the plasma duct taken through plane 7—7 of FIG. 2.

As shown in what may be termed side and end elevational views of FIGS. 2 and 3, the bowl is constructed to have a red cell reservoir 20 and a plasma reservoir 21 connected by one or more plasma ducts. In a preferred embodiment, two oppositely disposed plasma ducts 22 and 23 are used. The bowl is preferably formed of a blood-compatible plastic material such as a polycarbonate, polyethylene or polyurethane which may be flexible or rigid. The reservoirs 20 and 21 and ducts 22 and 23 may conveniently be made from two sheets of plastic which are heat sealed at an area of contact 25 surrounding red cell reservoir 20, an area of contact 26 between reservoirs 20 and 21 and around reservoir 21 and an area of contact 27 around the plasma ducts 22 and 23. Typically, this may be done by a twin sheet forming process wherein 2 sheets of plastic are heated and formed simultaneously so that heat sealing is accomplished at the same time the reservoirs and ducts are formed. Thus as will be apparent from FIGS. 2 and 3 the ducts are formed between sealed areas 26 and 27. These sealed areas of contact between the two vacuum-formed sheets of plastic, each of which defines one-half of each reservoir and each duct, are on a plane in the axis of rotation of the bowl.

In a preferred embodiment of the bowl of this invention, the plasma duct or ducts enter the tops of reservoirs 20 and 21 at a radius from the center of rotation 30 equal to about one-third of the outside radius of the reservoirs. This duct entrance radius should be greater for the plasma reservoir 21 than for the red cell reservoir 20 to ensure the flow of plasma from reservoir 20 into reservoir 21. In using the pheresis bowl of this invention to collect the plasma from 2 units of blood withdrawn from the donor, the red blood cell reservoir 20 will be constructed to have a working volume of about 250 milliliters and the plasma reservoir 21 to have a working volume of about 700 milliliters. As will be apparent from the detailed description of the process of this invention given below, the actual volumes of the reservoirs will be somewhat greater (by about as much as 20%) than their working volumes. In order to return essentially all of the red cells to the donor from red cell reservoir 20, this reservoir should have a drainage angle, $\alpha$ in FIG. 2, which is at least 5°. Drainage angles, e.g., 30° or more, which are considerably greater than this may, of course, be used and are, in fact, preferable.

The pheresis bowl of this invention rotates about its axis, e.g., axis 30 of FIG. 2 and it may be supported in close fitting shoes 65 and 66 (FIG. 20) which engage through bowl extension 31 with a chuck (not shown) associated with a suitable centrifuge drive system such as is well known in the centrifuge art. Flexible tubing 12 engages a rigid tubing 32 which passes to a rotary seal 33. Rigid tubing 32′ connects rotary seal 33 to bowl extension 31 through a flexible connector 34. Rigid tubing 32′ rotates with flexible connector 34 and rotor 10 whereas rotary seal 33, rigid rubing 32 and flexible tubing 12 remain stationary. A fluid passage is therefore provided from tubing 12 into reservoir 20; and thus there is continual fluid communication between the donor through stationary tubing 12 and spinning red cell reservoir 20.

The top of the pheresis bowl has a central passage 35 communicating with the top of the plasma reservoir 21. This passage 35 is connected with an external vent filter 36 adapted for introducing aseptic air into the bowl during discharge of the red blood cells from reservoir 20 as well as for releasing air from pheresis bowl 10 as blood flows into it. As will be seen in the description of FIG. 10, a preferable arrangement is to also provide an air passage into red cell reservoir 20.

The pheresis bowl of this invention is preferably, but not necessarily, constructed by blow molding with a preblow cycle which, in effect, forms an oversize plastic bubble. This bubble, in turn, assumes the symmetrical two halves 40 and 41 which become heat sealed together in areas 25, 26 and 27 as the two halves of the mold are closed against each other.

Figure 4:
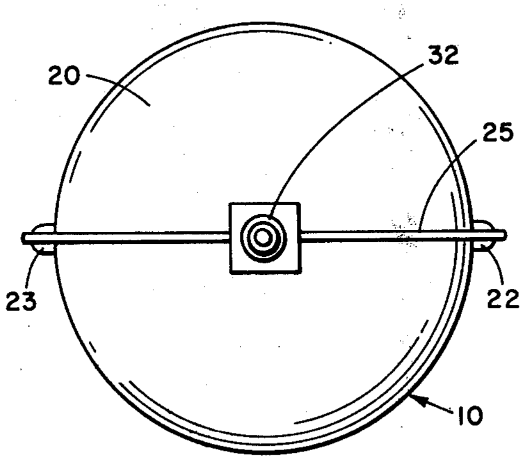
FIG. 4 is a bottom view of the disposable plasma pheresis bowl of FIGS. 2 and 3.

This construction is illustrated in detail in the fragmentary cross sections of FIGS. 5–8 which illustrate the construction of the embodiment of FIGS. 2–4. As will be seen in FIGS. 5–8 the two plastic halves 40 and 41 are molded to form front wall 42 and back wall 43 of plasma reservoir 21, (the terms "front" and "back" being used only for convenience of description), surfaces 44 and 45 which make up heat sealed contacting area 26, walls 46 and 47 of plasma duct 22 and surfaces 48 and 49 forming contacting area 27 which is also heat sealed. These two plastic halves 42 and 43 also form front and back walls 50 and 51 of the red cell reservoir and surfaces 52 and 53 which make up contacting area 25. A similar construction is conveniently used to form the entire bowl.

Figure 8:
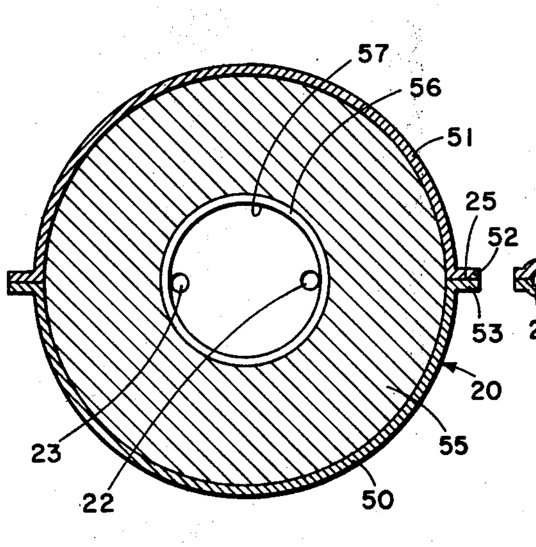
FIG. 8 is a cross section of the wall of the red cell reservoir taken through plane 8—8 of FIG. 2.
Figure 9:
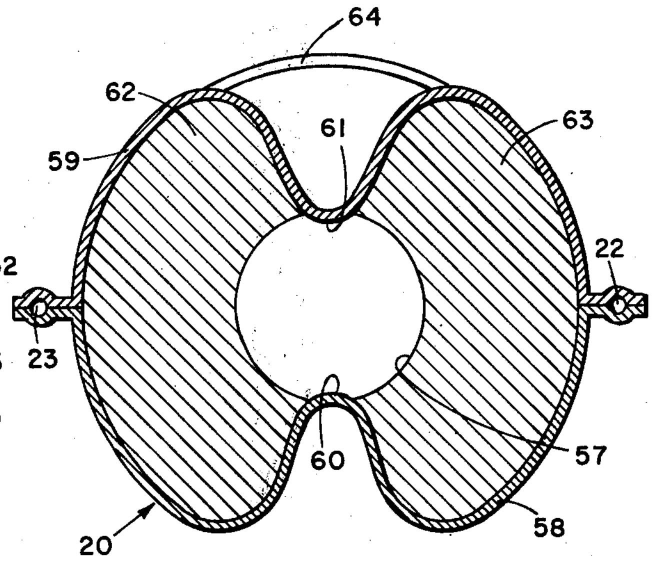
FIG. 9 is a cross sectional view of a modification of the plasma reservoir of the pheresis bowl of FIG. 2 taken through a section corresponding to plane 9—9 of FIG. 2.

FIG. 8 is a cross section of the red cell reservoir 20 illustrating the situation which obtains during centrifuging. In FIG. 8, the red blood cells are shown as the lightly cross-hatched mass 55 and the plasma as the liquid mass 56 contigious with the edge of plasma ducts 22 and 23. In this red cell reservoir the red cells as they build up assume an annularly-shaped mass. In the modification of FIG. 9, the plasma reservoir 21 has a cross sectional configuration best described as that of a "figure 8" or "pinch bottle." It is made of two centrally indented sections 58 and 59, perferably molded and heat sealed as previously described. The indentations in effect define internal re-entrant walls 60 and 61 which act to stop waves from building up at the plasma-air interface 57. The two plasma masses shown as lightly cross hatched areas 62 and 63 thus formed may be connected through an external tubing 64, to correct for any unbalance in the two red cell masses 62 and 63.

FIGS. 10–19 illustrate further embodiments of the pheresis bowl of this invention wherein there are incorporated additional means to insure the complete separation of red cells from plasma and means to eliminate any possibility of unbalance in operation. The apparatus embodiments illustrated in FIGS. 2–4 and 9 may, under some circumstances, exhibit an unwanted sensitiveness to rough operation, e.g., excessive vibration during operation. This in turn may give rise to the presence of some red cells in the plasma product in the plasma reservoir. The apparatus embodiments of FIGS. 10–19 insure smooth operation through the use of air vents to both reservoirs, the incorporation of a weir in the red cell reservoir and the use of a baffle in the plasma reservoir.

Figure 10:
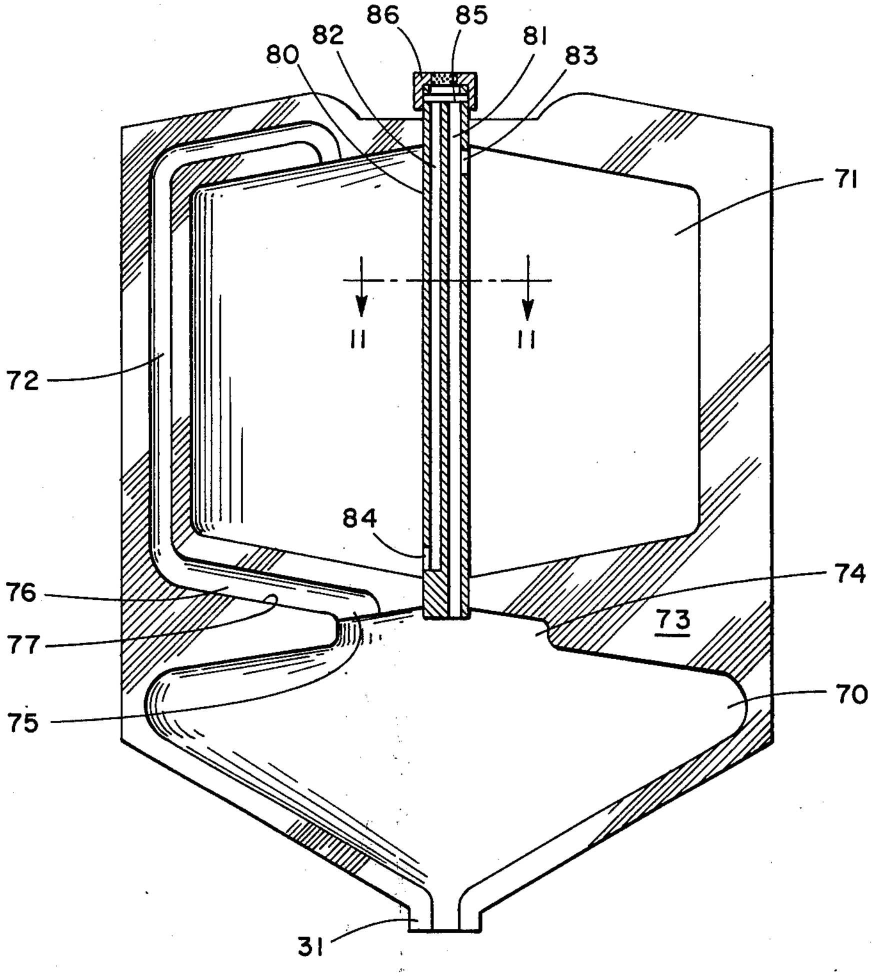
FIG. 10 is a front elevational view of one section of another embodiment of the pheresis bowl of this invention showing a modification in construction and the incorporation of a reservoir vent tube in cross section.

FIG. 10 is an elevational view of what may for convenience be termed the back half-section of another embodiment of the pheresis bowl of this invention. As in the case of the embodiment of FIGS. 2–4 it is preferrably formed by molding an appropriate type of synthetic plastic. In this half-section there are defined the back half of red cell reservoir 70, the back half of plasma reservoir 71, one of the two plasma ducts 72 (the other being defined on the other side of the mating front half-section) and a sealing/contacting member 73. Red cell reservoir 70 is configured to define a reentrant circular weir 74 at its upper discharge end, the purpose of which is to avoid any conditions which may lead to reentrainment of the separated cells. Such a reentrant weir minimizes the flow velocity in the plasma layer over the packed cells in lower red cell reservoir 70 so that any tendency to reentrain cells by the plasma is minimized. As a net result removal of cell-free plasma from the donor may be accomplished in a minimum period of time.

As will be seen in FIG. 10, it is also generally preferable that the entrance 75 to the duct passages (e.g., to duct 72 shown in FIG. 10) emerging from the red cell reservoir be large enough in cross section to prevent entrainment of any appreciable number of air bubbles in the plasma as it passes into the ducts. That is, to insure continuously smooth operation, any air bubbles in the entering plasma must immediately rise to the plasma air interface within the entry region of the passage so that a sufficient liquid column will form in the radial portion of this duct to more than counterbalance a full liquid leg in the full radial duct discharging into the top of the plasma reservoir. Typically, these ducts, e.g., duct 72 of FIG. 10, will have a diameter of about $\frac{1}{4}$ inch and they will be sloped through their lower radial section 76 such that the plasma will tend to be centrifuged against the lower wall 77 of this radial duct section 76 to allow free escape of air bubbles in the upper region of the entrance 75 of the duct. This escaping air will then pass inward toward the center of bowl rotation where it will join the air in the general vent air system described below.

Figure 12:
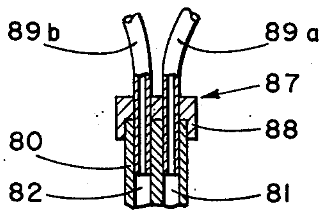
FIG. 12 is a cross sectional view of a two-pronged connector tube adapted for engagement with the upper end of the vent tube of FIG. 10.

The air vent system illustrated in cross section in FIGS. 10–12 represents one preferred embodiment of this apparatus component. When an air vent is provided for only the plasma reservoir as in the embodiment of FIG. 2 it may be necessary to apply a significant pressure on the feed into the red cell reservoir to overcome the tendency for slugs of liquid to block the ducts joining the reservoirs. Such pressure must overcome the centrifugal forces acting upon such slugs of liquid when the ducts are not full. The need for such feed pressure may be eliminated by an air vent system which provides separate, but interconnected, fluid communication means with both reservoirs.

In FIG. 10 the air vent means is shown to comprise an axially aligned tubing 80 defining parallel fluid channels or passages 81 and 82 drilled therein. Fluid passage 81 extends throughout tubing 80 providing fluid communication into red cell reservoir 70. Tubing 80 has an upper opening 83 into passage 81 located to provide fluid communication between passage 81 (and hence red cell reservoir 70) and the top part of plasma reservoir 71. Passage 82 terminates short of red cell reservoir 70 and tubing 80 has a lower opening 84 into passage 82 located to provide fluid communication between passage 82 and the bottom of plasma reservoir 71. Tubing 80 is sealed to weir 74, to the bottom and top of plasma reservoir 71 and between the sealing/contacting surfaces (e.g. surface 73 of the half-section of FIG. 10) where it extends between reservoirs 70 and 71 and where it extends beyond the top of reservoir 71. Tubing 80 terminates a short distance beyond the sealing/contacting edge of the bowl and is adapted at its upper end 85 to make connection with a conventional IV vent filter 86 to filter any atmospheric air which may enter the reservoirs by way of the passages of the vent. Connections may be made with passages 81 and 82 through a two-pronged connector 87 such as illustrated in FIG. 12. This connector has a cap 88 designed to make a tight fit around tubing 80 and two tubings **89*a* and 89*b* sized and positioned to be inserted into passages 81 and 82. Such a two-pronged connector may be used to drain plasma from plasma reservoir 71** if desired.

Figure 13:
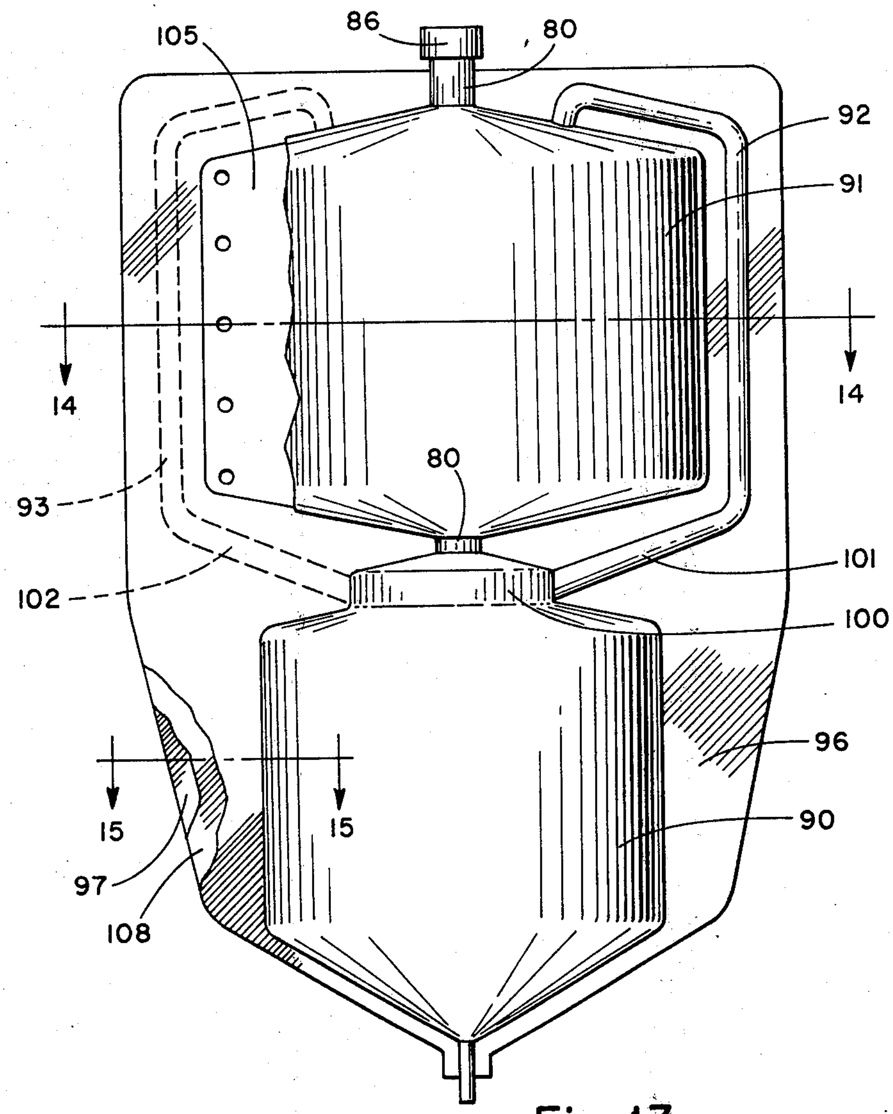
FIG. 13 is a front elevational view of another embodiment of the pheresis bowl of this invention illustrating the incorporation of a baffle plate in the plasma reservoir.
Figure 14:
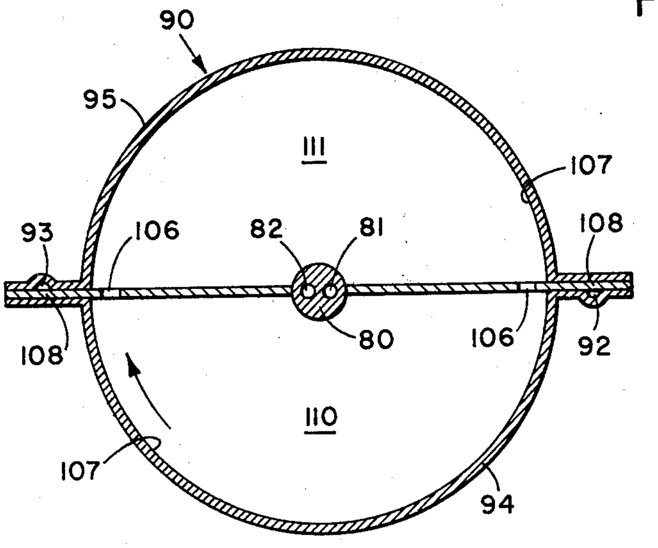
FIG. 14 is a cross section through the plasma reservoir of FIG. 13 taken through section 14—14 of FIG. 13.
Figure 15:
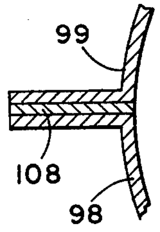
FIG. 15 is a fragmentary cross section through the red cell reservoir of FIG. 13 taken through section 15—15 of FIG. 13.

FIGS. 13–15 illustrate an embodiment of the pheresis bowl of this invention having a baffle within the plasma reservoir to accomplish balancing of the liquid within the reservoir. The use of a baffle replaces the "figure 8" plasma reservoir configuration shown in FIG. 9.

In the embodiment illustrated in front elevational view in FIG. 13 it will be seen that the basic structure of a red cell reservoir 90 and a plasma reservoir 91 joined through two oppositely positioned ducts 92 and 93 is retained. As will be seen in FIG. 14, which represents an exemplary form of construction for the pheresis bowl, duct 92 is defined by a lateral continuation of front wall 94 of reservoir 91 while duct 93 is defined by a corresponding lateral continuation of back wall 95 of reservoir 91. These front and back walls are of course continuous with front sealing/contacting surface means 96 and back sealing/contacting surface means 97, respectively, which in turn are also continuous with front wall 98 and back wall 99 forming red cell reservoir 90 (see FIG. 15). Red cell reservoir 90 is shown in FIG. 13 to have a circular reentrant weir 100 corresponding in construction and function to weir 74 of the pheresis bowl of FIG. 10. Likewise, ducts 92 and 93 have enlarged radial sections 101 and 102 as described for the bowl of FIG. 10; and the vent tubing 80 of FIG. 10 is incorporated in the bowl of FIG. 13.

The red cell reservoir 90 of FIG. 13 has a configuration different from the bowl embodiments of FIGS. 2 and 10. Thus the red cell reservoir 90 of FIG. 13 is somewhat more easily adapted for incorporation of an optional baffle system as described below in connection with the discussion of FIGS. 18 and 19. However, it will be apparent that the other red cell reservoir configurations described are also suitable for incorporation of a baffle system.

Within plasma reservoir 91 there is located a stiff flat center plastic wall 105 serving as a baffle means with a series of small perforations 106 located on both sides of the baffle means near the inner wall 107 of the plasma reservoir (FIG. 14). For ease of construction, the baffle plate may be formed by interposing a stiff flat plastic plate 108 between the front sealing/contacting member 96 and back sealing/contacting member 97, extending, as will be seen in FIGS. 13, 14 and 15, over the same area as members 96 and 97. Thus the baffle plate in the embodiment of FIGS. 13–15 is thermally welded into the pheresis bowl as it is molded, provision being made to cut the baffle plate to fit around and be sealed to central tubing 80 and to not extend into the red cell reservoir.

The small perforations 106 along the sides of baffle plate 105 eliminate any unbalance which might otherwise develop as a consequence of uneven filling of chambers 110 and 111 defined within plasma reservoir 90 (FIG. 14). Since during centrifugation the plasma will build up around the internal wall region of reservoir 91, the perforations 106 will attenuate any tendency of waves of liquid to be reflected back and forth between adjacent surfaces of the baffle plate 105 and will provide for equal distribution of the plasma between the two chambers 110 and 111.

It is also, of course, within the scope of this invention to use any other suitable technique for positioning a baffle means within plasma reservoir 91. One example of another suitable baffle means and manner of installing it is illustrated in FIGS. 16 and 17, FIG. 16 being a cross section through plasma reservoir 91 taken through a plane similar to section 14—14 of FIG. 13, and FIG. 17 being a cross section through plane 17—17 of FIG. 16.

Figure 16:
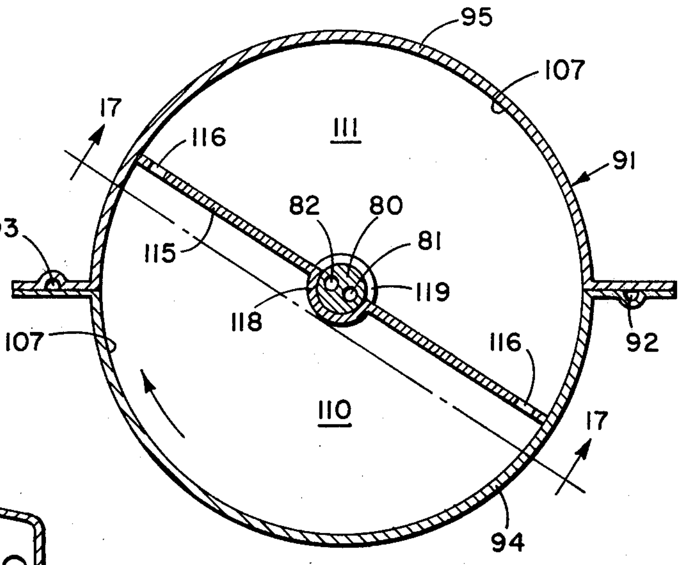
FIG. 16 is a cross section through the plasma reservoir of the FIG. 13 showing a modification of the baffle plate.
Figure 17:
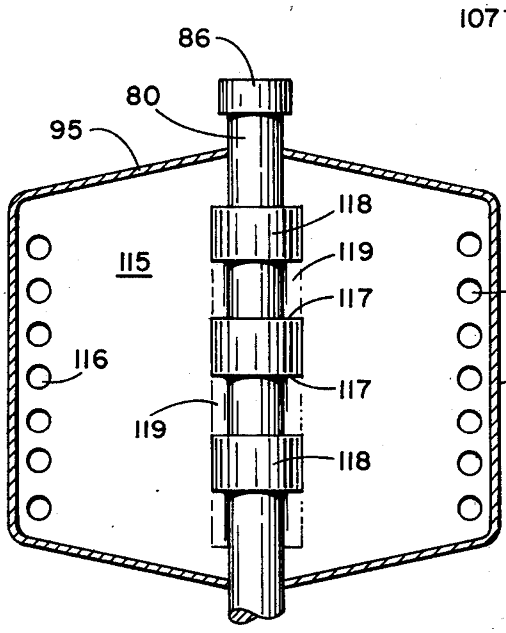
FIG. 17 is a front elevational view of the baffle plate of FIG. 16.

In the modification shown in FIGS. 16 and 17 baffle 115, with side perforations 116, is cut to fit the inside wall of reservoir 91 and is held in place by being fitted around vent tubing 80. This is conveniently accomplished by cutting a plurality of centrally located horizontal slots 117 in baffle 115 and forcing adjacent bands 118 and 119 thus formed in opposite directions to define a central passage through which tubing 80 is slipped to form a friction fit.

Figure 18:
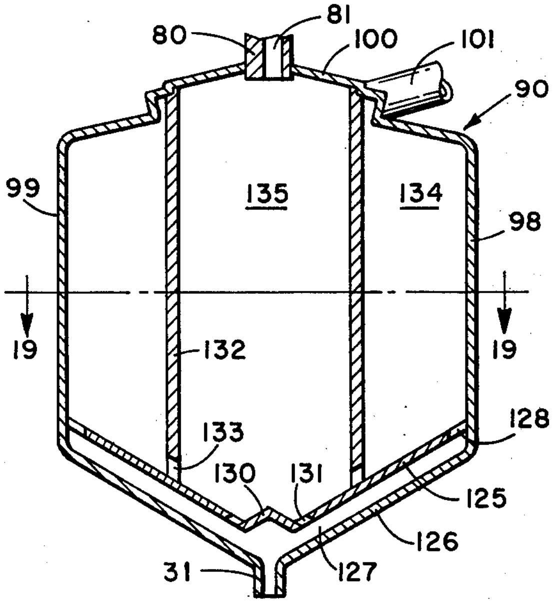
FIG. 18 is a longitudinal cross section of the red cell reservoir of the embodiment of FIG. 13 illustrating the incorporation of a baffle system within the red cell reservoir.
Figure 19:
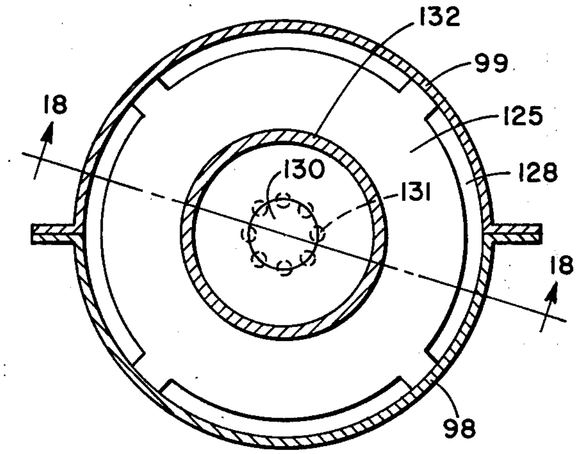
FIG. 19 is a transverse cross section of the red cell reservoir of FIG. 18 taken through section 19—19 of FIG. 18.

The red cell reservoir 90 of the embodiment of FIG. 13 may, if desired, also contain a baffle system shown in the cross sectional drawings of FIGS. 18 and 19 to comprise several baffle sections. The first of these baffle sections is a feed baffle 125 which generally parallels the bottom wall 126 of reservoir 90, defines a blood feed passage 127 therebetween and has peripheral fluid openings 128 providing fluid communication with the interior of reservoir 90. Feed baffle 125 is centrally configured to form a conically-shaped feed hood section 130 having a plurality of openings 131 providing fluid communication with fluid passage 133 connected to tubing 12 (See FIG. 2). The third section of the baffle system in red cell reservoir 90 comprises an axially aligned, hollow, cylindrical core section 132 resting on feed baffle 125 and having a plurality of fluid ports 133 providing fluid communication between the annular chamber 134 (defined between the inside wall of reservoir 90 and the outer wall of core 132) and the cylindrically-configured chamber 135 within core section 132.

The baffle means shown in FIGS. 18 and 19 for the lower red cell reservoir is optional. Its primary function is to insure balanced operation and to hasten the drainage of red cells from the reservoir for return to the donor once centrifugation is stopped. It is also, of course, within the scope of this invention to use a baffle system of a similar design in the red cell reservoirs of the pheresis bowl embodiments of FIGS. 2 and 10 and to construct the plasma reservoir associated with it in any of the ways previously illustrated and described.

In the operation of a pheresis bowl in which the red cell reservoir has a baffle system such as illustrated in FIGS. 18 and 19, the anticoagulant-containing blood from the donor entering the reservoir is forced through feed passage 127 and peripheral openings 128 into annular chamber 134. The red cells pack up against the outer internal wall of reservoir 90 while the liquid plasma enters the peripheral part of weir 100 and then the two radial sections of the ducts for transfer to the plasma reservoir. With the completion of delivery of blood from the donor, the centrifuge is stopped (preferably with a quick sudden braking action) and the red cells are returned down over the upper surface of feed baffle 125 through openings 133 and 131 into tubings 32 and 12.

Although the pheresis bowl of this invention has been illustrated and described in terms of the red cell reservoir's being positioned below the plasma reservoir, it is also, of course, within the scope of this invention to reverse this arrangement to have the plasma reservoir below the red cell reservoir so long as the bowl forms a unitary centrifuge rotor.

Figure 20:
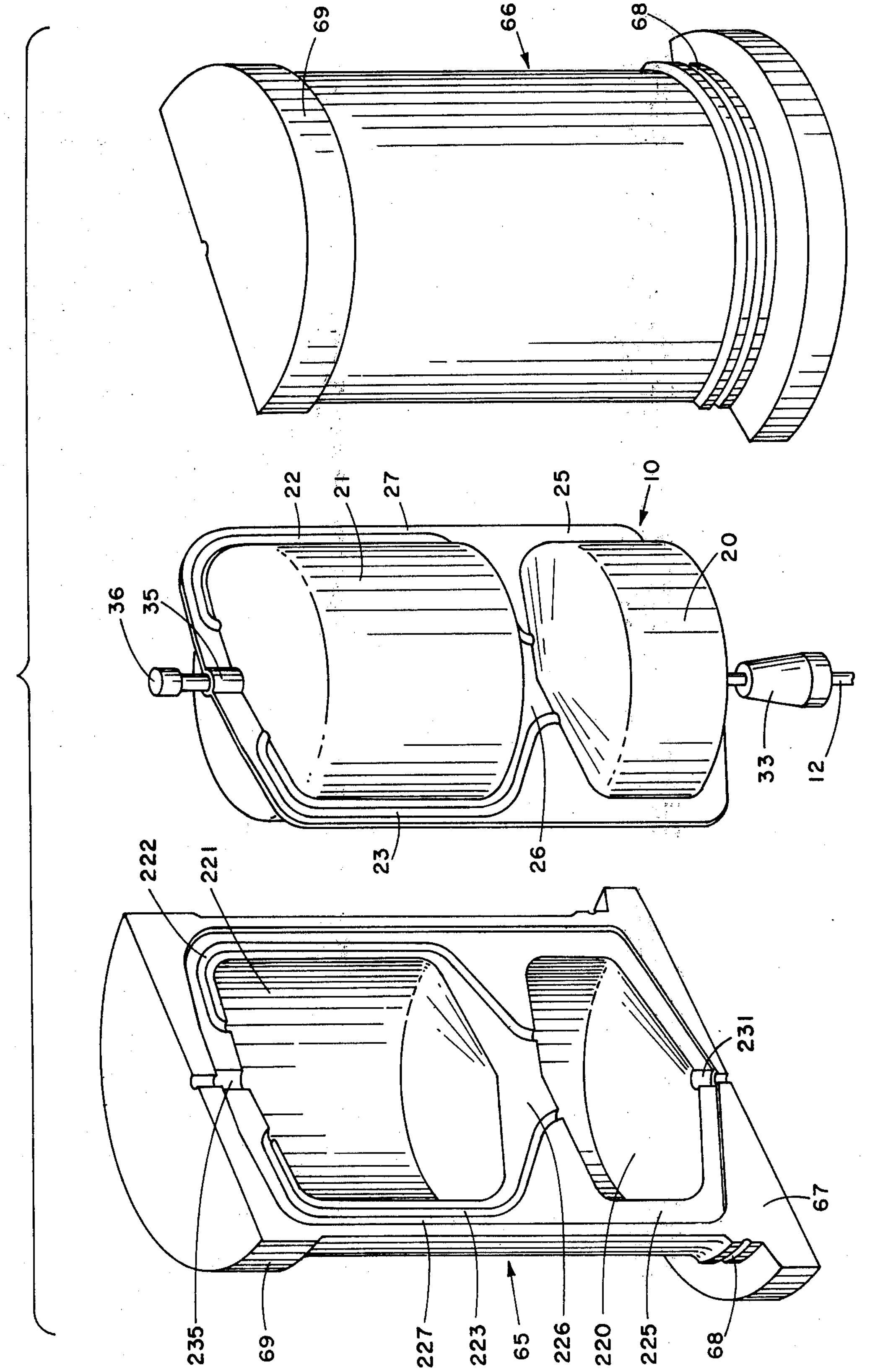
FIG. 20 is an exploded perspective view of the pheresis bowl and the two halves of a supporting shoe member.

If the pheresis bowl is not formed of sufficiently rigid plastics to make it self-supporting then it will be necessary to support it in a supporting shoe means such as shown in FIG. 20 wherein the two halves 65 and 66 of an exemplary support shoe are shown on either side of a pheresis bowl 10 such as is shown in FIGS. 2–4. Each shoe half is internally contoured to have cavities shaped to conform to one side of the external contours of the pheresis bowl. Thus, as will be seen in the case of shoe half 65, it has cavities 220 and 221 configured to fit the back walls of red cell reservoir 20 and plasma reservoir 21, and cavities 222 and 223 to fit the back walls of plasma ducts 22 and 23. This arrangement also prevails for the contacting surfaces, and passages.

The shoe halves are made to fit together through engaging surface 67, which essentially surrounds the pheresis bowl, and to be held in the engaged position by a suitable chuck (not shown). Externally the shoe, when assembled, may have a lower annular groove 68 arranged to seat an elastomeric ring suitable for effecting engagement with a chuck and an upper register surface 69 for maintaining alignment within a chuck. The internal contour of the shoe support means may also, of course, be made to fit any bowl embodiment, e.g., that of FIGS. 9, 10 and 13.

Figure 21:
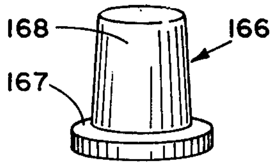
FIG. 21 is a side elevational view of the exterior of a modified shoe member.

Other external configurations of the supporting shoe for the bowl may also, of course, be used. One simple but effective shoe design is illustrated in FIG. 21. The shoe 166 shown in FIG. 21 has a base 167 and a bowl support section 168 with a very small (e.g. about 1°) taper angle. A bowl of this design may be secured by a simple friction grip in a centrifuge chuck having a matching taper angle.

The bowl shoe supports, such as shown in FIGS. 20 and 21, are preferably formed by molding a low-density, foamed plastic having a low modulus of elasticity. Such shoes are light in weight and offer relatively low moments of inertia in centrifuging.

The following operational example, assuming the use of the pheresis bowl embodiments of FIG. 13, is given to further describe the process and apparatus of this invention. The pheresis bowl is placed within its supporting shoe member, if used, and then the bowl and shoe member are set into the chuck of a centrifuge to provide a system as illustrated in FIG. 1. Anticoagulant is added continuously to the blood withdrawn from the donor and the anti-coagulated blood is metered through tubing 12 into red cell reservoir 90 by pump 14 and a rate of about 75 milliliters per minute while the bowl is rotated at about 4000 rpm. As the blood enters red cell reservoir 90, the air it displaces is forced out through passage 81 of vent 80 (FIG. 10). During centrifuging, the red cells pack up on the internal wall of red cell reservoir 90 while the plasma goes into the central part of reservoir 90. As the lower reservoir is filled a point is reached when the plasma spills over weir 100 and is carried up through ducts 92 and 93 into plasma reservoir 91. The radial sections 101 and 102 of ducts 92 and 93, respectively, are of sufficient diameter to allow an air gap above the plasma as it is forced by centrifugal action against the lower part of the internal walls defining radial sections 101 and 102. This air then passes through ducts 92 and 93 into plasma reservoir 91, through passage 83 in vent 80 and into the atmosphere through vent filter 86. Likewise, the air displaced by the plasma entering reservoir 91 is forced through passage 83, vent 80 and filter 86. There are, therefore, no air locks in the bowl during operation.

If, as in the preferred bowl embodiment described, the plasma reservoir has a baffle with side perforations, then any initial unequal distribution of the plasma between the two reservoir chambers 110 and 111 (FIG. 14 or 16) is corrected by virtue of the transfer of plasma from one chamber to the other through the baffle perforations. If the red cell reservoir has a baffle system such as shown in FIGS. 18 and 19, then the flow of cells and plasma is that described previously in connection with the description of these drawings.

In those pheresis bowl embodiments, such as shown in FIGS. 10–16, wherein the plasma ducts are formed on one or the other side of a center plane, e.g., a baffle, passing through the rotor axis, then the direction of bowl rotation during centrifuging is preferably such that the ducts are leading as indicated by the arrows in FIGS. 14 and 16. After the prescribed quantity of red cells has been accumulated in the red cell reservoir, rotation of the bowl is stopped, preferably with a sudden braking action. Such a braking action produces several desirable effects. Thus sudden braking will cause the plasma to pile up on the baffle in a manner to prevent its shloshing back into the lower red cell reservoir. Sudden braking will also immediately dislodge the red cells from the red cell reservoir wall to get them uniformly resuspended so that they will drain quickly from the red cell reservoir. This is important since it makes it possible to return the red cells to the donor before there is any clotting of any unanticoagulated blood in the phlebotomy needle.

The red cells are then returned to the donor by reversing the flow in the tubing 12 and in the phelbotomy needle 13. As the red cells are discharged, air enters the red cell reservoir through the vent system. A volume of saline or volume expander may be pumped via tubing 17 and pump 18 simultaneously with the cells to compensate for the loss of blood volume represented by the plasma. Plasma which has entered the plasma reservoir will not be pumped out during the return of the red cells to the donor because asceptic air enters through the vent filter and passes through the fluid passage to enter the red cell reservoir as the cells are pumped out. The pump control system may include suitable programming means (not shown) for stopping pump 14 before all of the cells have been pumped from red cell reservoir and bubble sensors (not shown) which will stop the reinfusion pump action if air appears in pump tube 12. Final emptying of red cell reservoir 90 may be accomplished by manual control of pump 14 for the last 25 mililiters or so of blood cells. Because red cell reservoir 90 is constructed to have a drainage angle (angle $\alpha$ a of FIG. 2) it is possible to return essentially all of the red cells to the donor. This is very important, particularly if a donor is to undergo the pheresis procedure at frequent intervals.

The cycle described can be repeated to yield additional units of plasma for each cycle. For example, the red cell reservoir and plasma reservoir may be so proportioned as to hold the equivalent of one "unit" of red cells (cells from one pint of whole blood) in the red cell reservoir and two "units" of plasma in the plasma reservoir, thus permitting two cycles per donor visit to obtain two "units" of plasma in the plasma reservoir.

Figure 22:
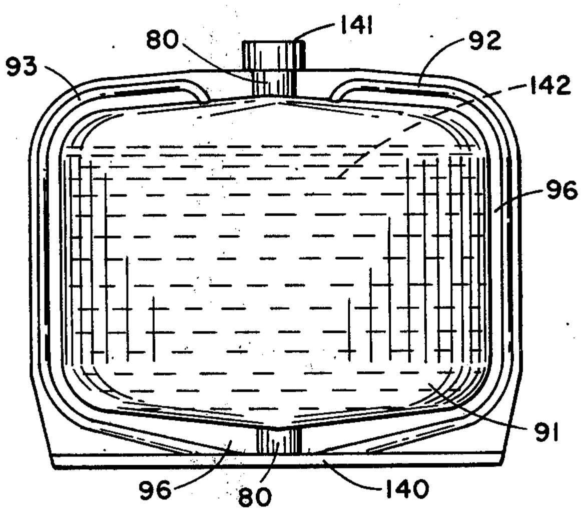
FIG. 22 is a side elevational view of a sealed plasma bowl ready for freezing.

Following the collection of one or two units of plasma, as many of the red cells as practical from the last unit are returned to the donor. The pheresis bowl containing the plasma in the plasma reservoir may then be taken to a heat-sealing machine to form a heat seal 140 (FIG. 22) between the red cell reservoir e.g., reservoir 90 of FIG. 13 and plasma reservoir 91 and across ducts 92 and 93 and vent tube 80 to seal them off. The vent filter is replaced by a sterile plug or cap 141. The red cell reservoir is cut off and discarded to leave the plasma reservoir and its contents 142 as shown in FIG. 22. The plasma reservoir may then be placed immediately in a suitable freezer designed for rapid freezing of the plasma in the shape of the plasma reservoir.

Alternatively to freezing the plasma in the original plasma reservoir, it may be desirable to transfer the plasma, subsequent to sealing off the plasma ducts and vent, to a plastic bag specifically designed for the purpose. Such plastic bags are typically thin-walled bags defining a relatively shallow container with relatively large surface area. The transfer of the plasma from the plasma reservoir of the pheresis bowl to a freezing bag may be accomplished by one of several techniques, using the two-pronged connector shown in FIG. 12 with the vent system detailed in FIG. 10. The vent filter 86 is removed and the two-pronged connector is placed on end 85 of the vent tube 89. In one mode of operation, that tubing of the two-pronged connector (e.g. tubing **89*b* of FIG. 12) which engages the passage (e.g., passage 82) providing fluid communication with the lower part of the plasma reservoir is connected to a source of sterile gas used to force the plasma through opening 83 and sealed off passage 81 into tubing 89*a* of the connector, tubing 89*a* being connected to a separate freezing bag. In another mode of operation tubing 89*b* may be a short tubing which terminates in a sterile air filter and the plasma reservoir is then tipped up to drain the plasma therefrom as sterile air enters tubing 89*b*** and through it into the interior of the plasma reservoir.

Frozen plasma in suitable containers may then be shipped to commercial plasma fractionation houses where the walls of the container can be aseptically peeled from the frozen blob of plasma. A large number of these blobs of frozen plasma then become the feed to a chain of processes used to fractionate out the antihemophilic factor and other useful fractions.

From the above description it will be apparent that the objects of the invention are attained and that the pheresis process and apparatus of this invention are safe, fast and economical.

It will thus be seen that the objects set forth above, among those made apparent from the preceding description, are efficiently attained and, since certain changes may be made in carrying out the above process and in the constructions set forth without departing from the scope of the invention, it is intended that all matter contained in the above description or shown in the accompanying drawings shall be interpreted as illustrative and not in a limiting sense.

I claim:

1. A unitary plasmapheresis centrifuge rotor, comprising, in combination:

a. a red cell reservoir in the shape of a centrifuge bowl, said reservoir having a bottom wall which defines a drainage angle of at least 5° and having a whole blood inlet and a plasma outlet;
b. a plasma reservoir in axial alignment with said red cell reservoir;
c. plasma duct means providing fluid communication between the plasma outlet of said red cell reservoir and said plasma reservoir;
d. air vent means communicating with said plasma reservoir; and,
e. means for engaging a centrifuge drive system whereby said centrifuge rotor can be spun to separate whole blood entering said red cell reservoir into a plasma component and a red cell component.

2. A unitary plasmapheresis centrifuge rotor in accordance with claim 1 wherein said red cell reservoir is positioned below said plasma reservoir.

3. A unitary plasmapheresis centrifuge rotor in accordance with claim 1 wherein said drainage angle in said red cell reservoir ranges between about 5° and about 30°.

4. A unitary plasmapheresis centrifuge rotor in accordance with claim 1 wherein sid red cell reservoir has internal baffle means.

5. A unitary plasmapheresis centrifuge rotor in accordance with claim 4 wherein said baffle means comprise a feed baffle section parallel with and spaced from said bottom wall of said red cell reservoir, a centrally positioned feed hood section and an axially aligned cylindrical core section, the chambers defined by said sections forming said baffle means being in fluid communication through fluid ports.

6. A unitary plasmapheresis centrifuge rotor in accordance with claim 5 wherein said red cell reservoir is formed to have a central cylindrical configuration.

7. A unitary plasmapheresis centrifuge rotor in accordance with claim 1 wherein said red cell reservoir has an upper, centrally positioned reentrant air through which said plasma duct means are joined to said red cell reservoir.

8. A unitary plasmapheresis centrifuge rotor in accordance with claim 7 wherein said plasma duct means comprise oppositely disposed ducts, each of which includes radial duct sections extending outwardly and at an upwardly directed slope from said reentrant weir of said red cell reservoir.

9. A unitary plasmapheresis centrifuge rotor in accordance with claim 8 wherein said radial duct sections are of larger diameter than the remaining portion of the duct length.

10. A unitary plasmapheresis centrifuge rotor in accordance with claim 8 wherein said upwardly directed slope of said radial duct sections is such as to cause plasma, during the rotation of said bowl, to be centrifuged against the lower walls of said radial duct sections and to define an air passage within said radial duct sections above said plasma.

11. A unitary plasmaphersis centrifuge rotor in accordance with claim 1 wherein the cross sectional configuration of said plasma reservoir taken normal to the axis of rotation of said bowl is similar to a figure eight thereby to define two oppositely disposed chambers within said plasma reservoir.

12. A unitary plasmapheresis centrifuge rotor in accordance with claim 11 including fluid communication means between said chambers.

13. A unitary phasmapheresis centrifuge rotor in accordance with claim 1 including means within said plasma reservoir to divide said reservoir into two chambers in fluid communication.

14. A unitary plasmapheresis centrifuge rotor in accordance with claim 13 wherein said means to divide said plasma reservoir into two chambers comprises a baffle extending through said plasma reservoir in a plane intersecting the axis of said rotor.

15. A unitary plasmapheresis centrifuge rotor in accordance with claim 1 wherein said duct means comprise oppositely disposed ducts.

16. A unitary plasmapheresis centrifuge rotor in accordance with claim 15 wherein said ducts are located on opposite sides of a center plane intersecting the axis of said rotor.

17. A unitary plasmapheresis centrifuge rotor in accordance with claim 15 wherein said plasma ducts communicate with the tops of said red cell and plasma reservoirs at a radius from the center of rotation of said bowl equal to about one-third the outside radius of said reservoirs.

18. A unitary plasmapheresis centrifuge rotor in accordance with claim 17 wherein said radius from the center of rotation is greater for said plasma reservoir than for said red cell reservoir.

19. A unitary plasmapheresis centrifuge rotor in accordance with claim 1 wherein said vent means also communicates with said red cell reservoir.

20. A unitary plasmapheresis centrifuge rotor in accordance with claim 19 wherein said vent means comprises tubing means extending from the upper part of said red cell reservoir through said plasma reservoir and terminating with a connecting end outside said plasma reservoir, said tubing means defining first and second parallel fluid passages both of which extend to said connecting end, said first passage providing fluid communication with said red cell reservoir and the upper part of said plasma reservoir and said second fluid passage providing fluid communication with the lower part of said plasma reservoir.

21. A unitary plasmapheresis centrifuge rotor in accordance with claim 20 including vent filter means affixed to said tubing means.

22. A unitary plasmapheresis centrifuge rotor in accordance with claim 1 wherein said red cell reservoir has a volume sufficient to contain the mass of red cells derived form one unit of whole blood and said plasma reservoir has a volume sufficient to contain the plasma derived form at least two units of whole blood.

23. A unitary plasmapheresis centrifuge rotor in accordance with claim 1 wherein the cross sectional configurations of said red cell and plasma reservoirs taken normal to the axis of rotation of said bowl are circular.

24. A unitary plasmapheresis centrifuge rotor in accordance with claim 1 further characterized as being formed from a blood-compatible synthetic resin material.

25. A unitary plasmapheresis centrifuge rotor in accordance with claim 24 wherein said bowl is formed as two half-sections which are then sealed to define said red cell and plasma reservoirs and said duct means.

26. A unitary plasmapheresis centrifuge rotor in accordance with claim 25 wherein said bowl is blow molded.

27. A unitary plasmapheresis centrifuge rotor in accordance with claim 1 including form-fitting shoe means to support said rotor during rotation and adapted for engagement with a centrifuge chuck.

28. A unitary plasmapheresis centrifuge rotor comprising, in combination:

a. a lower red cell reservoir in the shape of a centrifuge bowl, said reservoir having a bottom wall which defines a drainage angle of at least 5° and has a central opening suitable for engagement with tubing defining a fluid channel, said red cell reservoir having an upper centrally positioned reentrant weir;
b. an upper plasma reservoir in axial alignment with said lower red cell reservoir said plasma reservoir having means to divide it into two chambers in fluid communication;
c. oppositely disposed ducts providing fluid communication between said red cell reservoir and said plasma reservoir, each of said ducts including radial duct sections extending outwardly and at an upwardly directed slope from said reentrant weir of said red cell reservoir; and
d. vent means providing fluid communication between the ambient atmosphere and said red cell and plasma reservoirs and between said reservoirs.

29. A blood pheresis system, comprising in combination a. a plasma pheresis bowl as defined in claim 1;
b. phlebotomy needle means adapted for connection with a donor of whole blood and including means to admix an anticoagulant with said whole blood;
c. connecting means providing fluid communication between said red cell reservoir and said phelbotomy needle means, said connecting means comprising a flexible connector, a rigid tubing, rotary seal means and flexible tubing; and
d. pumping means associated with said flexible tubing for pumping anticoagulated whole blood from said donor into said red cell reservoir and for returning red cells from said red cell reservoir to said donor.

30. A blood pheresis system in accordance with claim 29 including means to admix saline solution or volume extender with said red cells during their return to said donor.

31. A blood pheresis system in accordance with claim 29 including shoe means configured to fit around and support said rotor and to be engaged with a centrifuge chuck.

* * * * *